US010751010B2

(12) United States Patent
Gemmel et al.

(10) Patent No.: US 10,751,010 B2
(45) Date of Patent: Aug. 25, 2020

(54) MOTION CONTROLLERS FOR MOBILE X-RAY DEVICES

(71) Applicants: Alexander Gemmel, Erlangen (DE); Gerhard Kleinszig, Forchheim (DE); Wei Wei, Forchheim (DE); Markus Weiten, Nürnberg (DE)

(72) Inventors: Alexander Gemmel, Erlangen (DE); Gerhard Kleinszig, Forchheim (DE); Wei Wei, Forchheim (DE); Markus Weiten, Nürnberg (DE)

(73) Assignee: Siemens Healthcare GmbH, Erlangen (DE)

( * ) Notice: Subject to any disclaimer, the term of this patent is extended or adjusted under 35 U.S.C. 154(b) by 287 days.

(21) Appl. No.: 15/633,991

(22) Filed: Jun. 27, 2017

(65) Prior Publication Data

US 2018/0008217 A1 Jan. 11, 2018

(30) Foreign Application Priority Data

Jul. 8, 2016 (DE) ...................... 10 2016 212 467

(51) Int. Cl.
*A61B 6/00* (2006.01)

(52) U.S. Cl.
CPC .......... *A61B 6/4405* (2013.01); *A61B 6/4441* (2013.01); *A61B 6/4476* (2013.01)

(58) Field of Classification Search
CPC ... A61B 6/4405; A61B 6/4441; A61B 6/4476; A61B 6/035; A61B 6/501; A61B 6/4007;
(Continued)

(56) References Cited

U.S. PATENT DOCUMENTS

| 5,386,453 A * | 1/1995 | Harrawood | A61B 6/0442 378/193 |
| 7,016,457 B1 * | 3/2006 | Senzig | A61B 6/032 378/116 |

(Continued)

FOREIGN PATENT DOCUMENTS

| CN | 1372870 A | 10/2002 |
| CN | 1623510 A | 6/2005 |

(Continued)

OTHER PUBLICATIONS

European Search Report for corresponding Application No. 17174052.5-1666, dated Dec. 1, 2017.

(Continued)

*Primary Examiner* — David P Porta
*Assistant Examiner* — Djura Malevic
(74) *Attorney, Agent, or Firm* — Lempia Summerfield Katz LLC

(57) ABSTRACT

The disclosure relates to a mobile X-ray device having an equipment cart that is movable on wheels and has a lifting device on which a support assembly is arranged. A C-arm is mounted to the support assembly so as to be displaceable along the circumference of the support assembly, wherein the C-arm has an X-ray source and an X-ray receiver arranged opposite the X-ray source. In order to simplify the handling of a mechanical zoom on mobile X-ray devices, a motion controller is provided by which, in any given pose of the C-arm, a movement of the C-arm is controlled in such a way that the central axis extending between X-ray source and X-ray receiver is fixed in space.

10 Claims, 1 Drawing Sheet

(58) Field of Classification Search
CPC ....... A61B 6/545; A61B 6/547; A61B 6/5241; A61B 6/587; A61B 6/508
See application file for complete search history.

(56) References Cited

U.S. PATENT DOCUMENTS

| | | | | |
|---|---|---|---|---|
| 7,338,207 | B2* | 3/2008 | Gregerson | A61B 6/032 378/17 |
| 7,500,783 | B2* | 3/2009 | Kalender | A61B 6/032 378/197 |
| 7,837,385 | B2* | 11/2010 | Klingenbeck-Regn | A61B 6/102 378/197 |
| 8,848,874 | B2* | 9/2014 | Kargar | A61B 6/102 378/117 |
| 9,808,211 | B2* | 11/2017 | Yorkston | A61B 6/032 |
| 9,833,215 | B2* | 12/2017 | Stopp | A61B 6/4452 |
| 2001/0022834 | A1* | 9/2001 | Graumann | A61B 6/4405 378/198 |
| 2001/0027263 | A1* | 10/2001 | Zylka | A61B 6/12 600/9 |
| 2001/0036246 | A1* | 11/2001 | Graumann | A61B 6/0478 378/39 |
| 2003/0099328 | A1* | 5/2003 | Jensen | A61B 6/08 378/198 |
| 2004/0066906 | A1* | 4/2004 | Hornegger | A61B 6/02 378/197 |
| 2005/0117706 | A1 | 6/2005 | Powell | |
| 2006/0293582 | A1* | 12/2006 | Jensen | A61B 6/08 600/407 |
| 2007/0211847 | A1* | 9/2007 | Graumann | A61B 6/102 378/15 |
| 2007/0211863 | A1* | 9/2007 | Graumann | A61B 6/4405 378/197 |
| 2008/0118036 | A1* | 5/2008 | Jensen | A61B 6/4441 378/198 |
| 2009/0274271 | A1* | 11/2009 | Pfister | A61B 6/12 378/62 |
| 2012/0099697 | A1* | 4/2012 | Helm | A61B 6/02 378/4 |
| 2012/0099778 | A1* | 4/2012 | Helm | A61B 6/4476 382/132 |
| 2012/0224673 | A1 | 9/2012 | Barker | |
| 2012/0281812 | A1* | 11/2012 | Noda | A61B 6/4233 378/62 |
| 2013/0083894 | A1* | 4/2013 | Niebler | A61B 6/4441 378/62 |
| 2013/0243160 | A1* | 9/2013 | Graumann | A61B 6/54 378/91 |
| 2013/0287171 | A1* | 10/2013 | Hibino | A61B 6/4405 378/62 |
| 2015/0085986 | A1* | 3/2015 | Dinse | A61B 6/10 378/98 |
| 2015/0131775 | A1* | 5/2015 | Yorkston | A61B 6/032 378/17 |
| 2015/0305703 | A1* | 10/2015 | Kim | A61B 6/467 378/62 |
| 2017/0290559 | A1 | 10/2017 | Gemmel et al. | |

FOREIGN PATENT DOCUMENTS

| | | |
|---|---|---|
| CN | 102652673 A | 9/2012 |
| DE | 10153787 A1 | 5/2003 |
| DE | 102006055165 A1 | 5/2008 |
| DE | 102014219436 A1 | 3/2016 |

OTHER PUBLICATIONS

Chinese Office Action for Chinese Application No. 201710549841.1 dated Nov. 30, 2018, with English translation.

German Office Action for German Application No. 102016212467.6, dated Apr. 4, 2017, with English Translation.

* cited by examiner

MOTION CONTROLLERS FOR MOBILE X-RAY DEVICES

The application claims the benefit of German Patent Application No. DE 10 2016 212 467.6, filed Jul. 8, 2016, which is hereby incorporated by reference in its entirety.

TECHNICAL FIELD

The disclosure relates to a mobile X-ray device having an equipment cart that is movable on wheels and has a lifting device on which a support assembly is arranged, on which support assembly a multiaxially adjustable C-arm may be mounted so as to be displaceable along its circumference, (e.g., so as to be rotatable about a center of rotation), wherein the C-arm has an X-ray source at one of its ends and an X-ray receiver arranged opposite the X-ray source. These X-ray devices may be used to reconstruct 3D images of a part of a patient's body from a series of 2D projections of the part of the body taken from different projection angles.

The disclosure further relates to a method for moving a mobile X-ray device and also to a computer program.

BACKGROUND

When mobile C-arm X-ray devices are deployed, it is necessary to set the position of X-ray source and X-ray receiver in such a way that the region of the body that is to be studied is represented on as large a scale as possible in the X-ray image. In other cases, it is desired to record images of an examination subject at different magnifications. In such cases, the size of the subject changes with the distance between subject and X-ray receiver.

In order to adjust the image range, the equipment cart is initially directed adjacent to the patient table and the C-arm is placed in relation to the patient table such that a smallest possible distance exists between subject and X-ray receiver. This is done in order to obtain as great an overview as possible of the overall anatomy, to localize the subject of interest, and to represent the same in the center of the image. If necessary, the subject is then increased or reduced in size in the image or image field of view. This is accomplished by an actuation of the lifting device, which in most cases takes the form of a lifting column that is often already motorized. The image field of view is in this case magnified by raising the C-arm and reduced by lowering the C-arm. In this way, a kind of zoom function is realized, this being referred to hereinafter as a "mechanical" zoom in order to distinguish it from the electronic zoom function within the recorded image.

Unlike in the case of stationary X-ray devices, (e.g., floor-mounted or ceiling-mounted X-ray devices), in which the distance between the X-ray source and the X-ray receiver is variable, the problem that arises with mobile C-arm X-ray devices, in which the distance between the X-ray source and the X-ray receiver may not be changed, is that the subject remains in the center of the image only in a strict AP (anterior/posterior) position of the C-arm, (e.g., an exactly vertical orientation of the C-arm), in which angulation angle and orbital angle are each zero, when the lifting column is raised or lowered, because the movement then takes place along the central axis. If the position (pose) of the C-arm diverges therefrom, e.g., if the C-arm is positioned at an angle (e.g., orbital/angulation angle is nonzero), it is not just the zoom, (e.g., the scaling factor), that changes as the lifting column is raised or lowered, as is desired, but also the position of the subject in the image. The central axis moves outward away from the subject. The subject wanders around in the image or even strays outside of the image.

This problem was solved in the prior art by correctively adjusting the C-arm position manually when performing enlargements with the aid of the mechanical zoom in order to re-center the subject in the image.

SUMMARY AND DESCRIPTION

The scope of the present disclosure is defined solely by the appended claims and is not affected to any degree by the statements within this description. The present embodiments may obviate one or more of the drawbacks or limitations in the related art.

It is an object of the disclosure to simplify the handling of the mechanical zoom on mobile X-ray devices. This object is achieved by a mobile X-ray device, by a method, or by a computer program.

The advantages and embodiments explained hereinbelow in connection with the mobile X-ray device also apply analogously to the method and the computer program, and vice versa.

A motion controller is provided by which, in any given initial pose of the C-arm, a movement of the C-arm is controlled in such a way that the central axis extending between X-ray source and X-ray receiver is fixed in space and remains so.

What is generally understood by a pose is the position and orientation of an object in space. The (relative) pose of the C-arm referred to herein signifies the relative position and orientation, more precisely the location of the C-arm with respect to the C-arm support assembly, which may be raised and lowered with the aid of the lifting device. The terms position and pose are sometimes used synonymously hereinbelow. The same applies to the terms lifting device and lifting column, where the vertical lifting movement of the C-arm holder, and thus of the C-arm itself, may also be realized with the aid of a device other than a lifting column, e.g., the lifting column is in this context to be regarded as merely by way of example.

What is understood by the central axis is the beam central axis, e.g., the central axis of the X-ray beam bundle emitted by the X-ray source.

One concept of the disclosure is to keep the subject of which the X-ray images are to be acquired in the central beam at all times. This is realized by moving the C-arm, as carrier of X-ray source and X-ray receiver, in a suitable manner for this purpose. The movement may be a movement of the equipment cart (and hence of the support assembly and the C-arm) in the horizontal direction and/or a movement of the C-arm in the vertical direction, brought about by the raising or lowering of the support assembly by the lifting column. For this purpose, it is provided that the corresponding moving mechanisms or devices possess motorized drives and that the drives are suitably actuated by a motion controller. Because the movement is motorized, it is possible to provide an automatable counterbalancing or compensating movement, e.g., in the form of a corrective adjustment or position correction of the C-arm. This also corresponds to the embodiments described herein.

It is also possible to keep the subject permanently in the central beam by moving the subject in a manner suitable for this, e.g., by a movement of the patient table in the horizontal and/or vertical direction. With the arrangement described here, (e.g., with the use of an X-ray device that is mobile in any case and has a motor-driven lifting column and motor-drivable wheels), the solution described as advantageous that does not involve a movement of the subject is realizable more easily and with less investment of effort than the considerably more complicated corrective adjustment of the, for example, very heavy patient table.

In an embodiment, the control of the movement of the C-arm in such a way that the central axis maintains its position in space is effected exclusively during the execution of the mechanical zoom described in the introduction, e.g., in the case of a movement of the X-ray receiver toward the subject or away from the subject, that is to say while the X-ray receiver is moved toward the subject (zoom out) or away from the subject (zoom in). The compensating movement may not take place during other periods. In particular, no horizontal displacement of the equipment cart takes place at such times, in particular for safety reasons.

According to an embodiment, the controlled movement of the C-arm is a vertical and/or horizontal positioning movement of the C-arm. Solely a vertical and/or horizontal positioning movement of the C-arm may be performed, (e.g., no other compensating movement). In particular, only the lifting column and/or the drive wheels are then actuated, while the position of the C-arm relative to the support assembly remains unchanged.

In a particular embodiment, a mobile X-ray device is provided in which, in any given pose of the C-arm, if there is a movement of the X-ray receiver toward the subject or away from the subject, a vertical and/or horizontal positioning movement of the C-arm are/is performed in such a way that the central axis is fixed in space or maintains its position in space.

An automatic correction of the position of the subject in the image may be achieved with the aid of the embodiments disclosed herein. A complicated and laborious actuation of various axes of the C-arm is not necessary for this purpose. Each time a mechanical zoom is initiated, (e.g., by raising or lowering the lifting column), a corresponding horizontal positioning movement of the C-arm takes place, such that the subject is kept in the central beam at all times and therefore appears centered in the image. This compensating movement of the C-arm may be performed synchronously, in the sense of simultaneously, or asynchronously, e.g., with a not insignificant time difference. Even an asynchronous compensating movement is acceptable provided the time instant at which the actual X-ray is taken is coordinated therewith, e.g., the X-ray image is recorded only when the compensating movement has been completed.

With the aid of an X-ray device having motorized wheels it is possible to adjust the C-arm position automatically, in particular the location of the C-arm in space while the orientation remains constant. The subject may be kept in the central beam at all times by a suitable movement of the C-arm. Lifting column and/or wheel position are/is changed so as to provide that the central beam has a fixed position in space. To put it another way, the C-arm is moved with the aid of a motorization of the lifting column and the driven wheels such that the mechanical zoom movement takes place along the central axis, regardless of the pose of the C-arm. The wheels may be a number of omnidirectionally drivable wheels or a number of other wheels with suitable drives. The point is that the equipment cart, and consequently the C-arm fixedly mounted thereon, may be moved in any desired direction of travel, e.g., forward and backward as well as sideways. A free maneuverability in all directions is important for the desired compensating or correction movement of the C-arm in such cases when angulation angle and orbital angle of the C-arm pose are nonzero. The motorized drives of the lifting column or wheels may be precisely controllable servo motors or stepper motors.

Depending on the initial pose, the C-arm is actuated and moved in different ways. In a first special case of a strict AP pose (e.g., vertical C-arm), only the lifting column is actuated. In another special case of a strictly lateral pose (e.g., horizontal C-arm), only the wheels are driven.

The disclosure proceeds based on a situation in which a specific initial pose of the C-arm is predefined. In this case this may be the AP pose or else an arbitrary other (e.g., "oblique") pose. The (e.g., controlled) movement of the C-arm, which is accomplished in the special manner described herein, therefore relates in each case to such a pose of the C-arm and takes place during the (e.g., unchanged) presence of such a C-arm position. In other words, it is taken as a premise that the C-arm has assumed a specific orientation, that is to say is aligned in the imaging direction, e.g., the position of the angles of rotation (e.g., angular-orbital) is certain and also no further pivoting, rotational or tilting movements of the C-arm itself are effected otherwise, e.g., the controlled movement of the C-arm includes a vertical and/or horizontal positioning movement of the C-arm.

Such a further movement of the C-arm is then controlled in a way that provides that the central axis is fixed in space. This is relevant, in particular, to the case of a movement of the X-ray receiver toward the subject or away from the subject, as is the case with a mechanical zoom. Such a movement may be effected as a result of a height adjustment by the lifting column, in other words a vertical positioning movement of the C-arm. Alternatively, it is also possible that such a movement of the X-ray receiver toward the subject or away from the subject is realized as a result of the subject itself being moved, e.g., by a raising or lowering of the patient table. In this case too, the central axis remains fixed in space. The vertical and/or horizontal positioning movement of the C-arm is controlled in such a way that the central axis maintains its position in space. As a result, this means that the movement toward the subject or away from the subject takes place along the (e.g., space-fixed) central axis.

The vertical and/or horizontal positioning movement of the C-arm may be an indirect positioning movement. This means that the C-arm itself is not moved in its support assembly, e.g., it maintains its pose. The C-arm is nevertheless moved relative to the subject in that the equipment cart complete with support assembly and C-arm and/or the support assembly together with the C-arm are/is moved by way of the lifting column.

In an embodiment, such a motion controller is realized by a corresponding drive controller for controlling the motorized drive of the lifting column as well as a corresponding drive controller for controlling the motorized drive of the wheels, whereby the motorized drive of the lifting column or, as the case may be, the motorized drive of the wheels is actuated automatically while the space-fixed central axis is maintained. The last-mentioned possibility, in particular, is of interest when the mechanical zoom is used. The mechanical zoom effected by a raising or lowering of the C-arm by the lifting column is performed thereby in such a way that the subject is kept in the central axis, (e.g., does not drift out of the image), because the movement of the X-ray detector toward the subject or away from the subject takes place along the central axis owing to the corresponding synchronous correction movement, namely the horizontal positioning movement of the C-arm by the driven wheels. In this case the direction of movement is therefore identical to the direction of the central beam. This corresponds to the embodiments disclosed herein.

The disclosure proposes a position correction or a corrective adjustment of the C-arm as a result of and during the mechanical zoom, e.g., the movement of the X-ray receiver toward the subject or away from the subject. In other words, the C-arm is correctively adjusted in accordance with the zoom movement, (e.g., synchronously with the zoom movement), in such a way that at any time instant the subject region of interest (ROI) lies within a beam cone of the X-ray beam bundle. The displacement of the central axis relative to the examination subject is counteracted or compensated for by the compensating movement of the C-arm (or of the subject or patient table), such that the same subregions of the examination subject may always be irradiated by the X-ray radiation or, as the case may be, the central beam extends through the examination center even at different positions of the mechanical zoom.

The positioning paths that are to be traversed by the lifting column and the equipment cart in the vertical and horizontal direction respectively for the purpose of the position correction of the C-arm are predefined by the motion controller as a function of the vertical and horizontal positioning movements that the C-arm performs as a result of and during the mechanical zoom. The necessary information is made available to the motion controller for this purpose. This information may be for example positional data of the equipment cart or the support assembly, or control information. In an embodiment, the actual zoom movement of the X-ray receiver is therefore determined initially, for example in the form of a vertical raising or lowering movement. Subsequently or synchronously with respect to time, the compensation is achieved by the corresponding counteracting or compensating movement, controlled using the data of the zoom movement.

The handling of the mechanical zoom on mobile X-ray devices is simplified considerably. In particular, an X-ray device operating fully automatically (at least in respect of the mechanical zoom) may be provided, which is implemented not in the conventional manner as a stationary component, (e.g., fixedly mounted to ceiling, wall or floor at the installation site), but as a mobile unit, in particular one that is capable of traveling across the floor in any directions.

Insofar as the motion controller may be realized in or by a data processing unit, the data processing unit may have a number of function modules, each function module being embodied to perform a specific function or a number of specific functions in accordance with the described method. The function modules may be hardware modules or software modules. In other words, the embodiments, insofar as they relate to the data processing unit, may be realized either in the form of computer hardware or in the form of computer software or in a combination of hardware and software. If the disclosure is implemented in the form of software, (e.g., as a computer program), all of the described functions are realized by computer program instructions when the computer program is executed on a computer having a processor. In this case, the computer program instructions are realized in a manner known per se in any desired programming language and may be provided to the computer in any desired form, for example in the form of data packets that are transmitted over a computer network, or in the form of a computer program stored on a diskette, a CD-ROM, or another data medium.

BRIEF DESCRIPTION OF THE DRAWINGS

The above-described characteristics, features, and advantages of the present disclosure, as well as the manner in which these are achieved, will become clearer and more readily understandable in connection with the following description of the exemplary embodiments, which are explained in more detail with reference to the drawings, in which.

All the figures illustrate the embodiments merely schematically. Like reference signs correspond therein to elements of like or comparable function.

DETAILED DESCRIPTION

Figure 1:
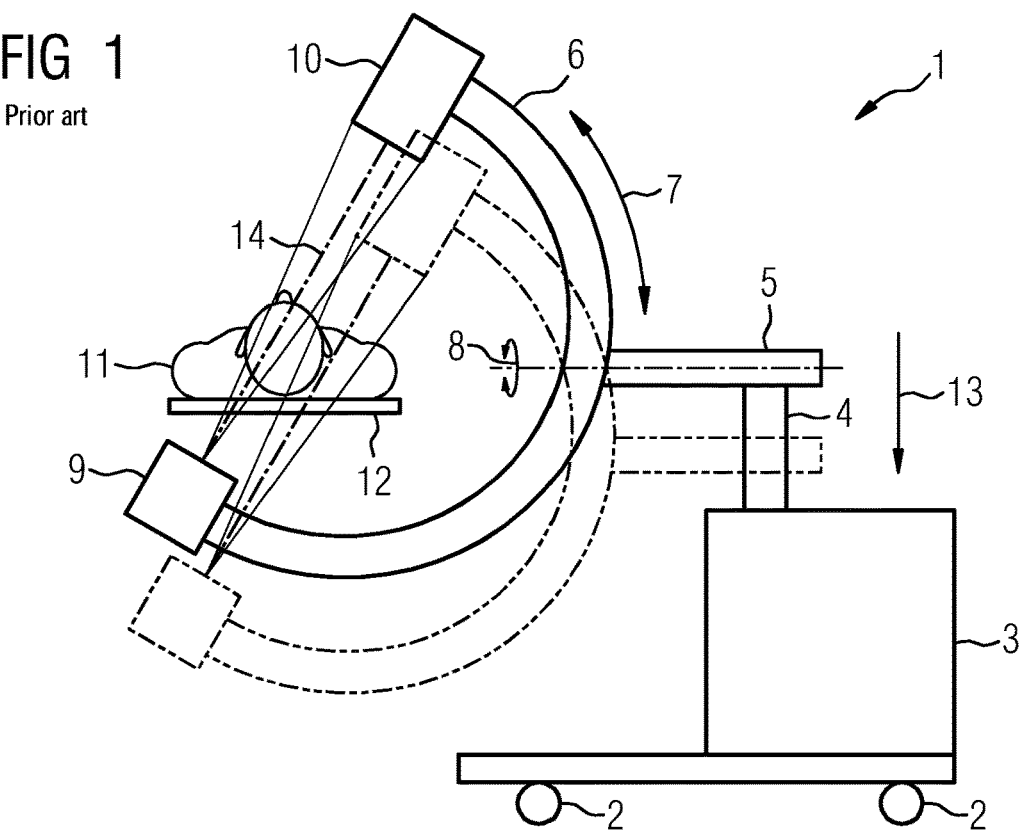
FIG. 1 depicts a mechanical zoom in the case of an X-ray device with C-arm according to the prior art.
Figure 2:
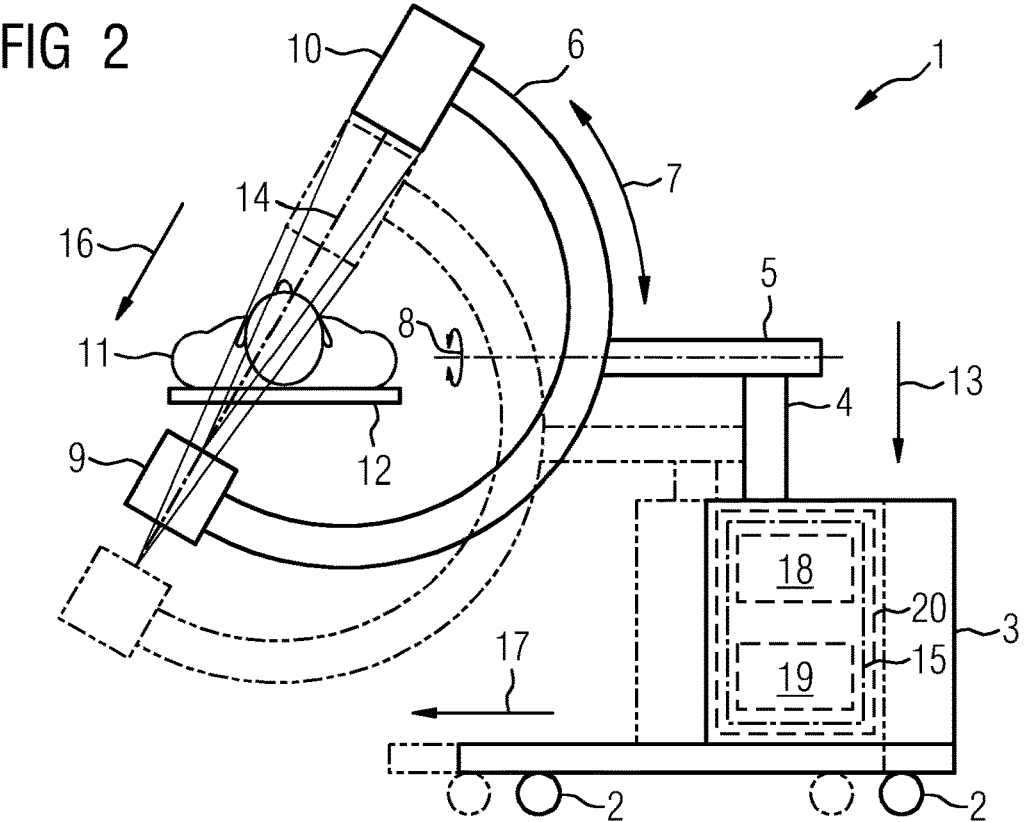
FIG. 2 depicts an example of a mechanical zoom in the case of an X-ray device with C-arm.

FIGS. 1 and 2 depict a mobile X-ray device 1 having an equipment cart 3 that is movable on wheels 2. The equipment cart 3 has a lifting device in the form of a lifting column 4 on which a support assembly 5 is arranged. A multiaxially adjustable C-arm 6 that is rotatable about a center of rotation (e.g., orbital angle 7) is mounted on the support assembly 5 so as to be displaceable along its circumference (e.g., angulation angle 8). The C-arm 6 has an X-ray source 9 at one of its ends and an X-ray receiver 10 arranged opposite the X-ray source 9. The C-arm 6 is placed close to a subject 11 that is to be examined, the examination subject 11 being, for example, a part of a patient's body. The subject 11 is placed on an examination table 12. The C-arm 6 is set at an angle. The orbital angle 7 and the angulation angle 8 are nonzero and consequently define the initial pose of the C-arm 6 relative to the support assembly 5.

In the present exemplary case, a zoom-out is to be performed. Starting from a great distance between the subject 11 and X-ray receiver 10, when a mechanical zoom is performed, this being realized by a motorized vertical lowering of the C-arm 6 with the aid of the lifting column 4, the distance between the X-ray receiver 10 and the subject 11 is reduced. Such a vertical movement 13 is labeled with an arrow. The starting position, where there is a great subject distance, is represented by solid lines, and the end position following termination of the mechanical zoom, where there is a small subject distance, is represented by broken lines. In the solution illustrated in FIG. 1, such as is known from the prior art, the position of the subject 11 in the image changes. The central axis 14 moves outward out of the subject 11.

This is not the case in the solution illustrated in FIG. 2, because the wheels 2 are drivable by motor and controllable in terms of their direction of travel, and a synchronous compensating movement of the C-arm 6 takes place using a corresponding motion controller 15, such that the central axis 14 is and remains stationary. The subject 11 is therefore kept in the central axis 14. The zoom movement 16 of the C-arm 6 takes place along the central axis 14.

The compensating movement of the C-arm 6 is accomplished by way of a horizontal displacement of the equipment cart 3, symbolized by arrow 17 in FIG. 2. The positioning movement 17 of the equipment cart 3 is executed in this case as a function of the length of the vertical lift during the mechanical zoom in respect of the path to be traversed, and as a function of the lifting direction (e.g., raising or lowering) and the pose of the C-arm (e.g., orbital angle 7 and angulation angle 8) in respect of the direction in which the equipment cart 3 is to be displaced.

Both the lifting column 4 and the wheels 2, which are alignable in respect of their direction of travel, possess electric motor drives in the form of servo motors that are connected to a motion controller. The motion controller 15 is realized as a computer program executed in a computing device 20, the computing device 20 may be part of the central control unit of the X-ray device 1. The required information is merged in the motion controller 15. The corresponding control signals for the drives are also generated in the motion controller 15. For this purpose, the motion controller 15 includes a first drive controller 18 for controlling the motorized drive (not shown) of the lifting column 4 and a second drive controller 19, cooperating with the first drive controller 18, for controlling the motorized drive (not shown) of the wheels 2. The drive control function is accomplished here in each case while maintaining the space-fixed central axis 14, the two drive controllers 18, 19 exchanging the information necessary for this.

One concept outlined here is to provide a compensating movement of the C-arm 6 in the case of a mechanical zoom, e.g., an increase or decrease in the size of the image field of view by a raising or lowering of the C-arm 6 by the lifting column 4, in such a way that the central axis 14 remains fixed in space, such that the subject 11 is not shifted in the image. To that end, motor-driven wheels 2 are used, with the aid of which the equipment cart 3 is repositioned in accordance with the required compensating movement. It applies that the subject 11 may be maintained in the central axis 14 at all times. This is accomplished by moving the associated axes of the C-arm 6 as a function of its initial pose.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A mobile X-ray device comprising:
an equipment cart that is movable on wheels and having a lifting device;
a support assembly arranged on the lifting device;
a C-arm mounted on the support assembly so as to be displaceable along a circumference of the support assembly, wherein the C-arm has an X-ray source and an X- ray receiver arranged opposite the X-ray source, and wherein a central axis extends between the X-ray source and the X-ray receiver for a given pose of the C-arm; and
a motion controller configured to control, for the given pose of the C-arm, a vertical positioning movement of the C-arm and a horizontal positioning movement of the C-arm such that the central axis extending between the X-ray source and the X-ray receiver remains fixed in space,
wherein the vertical positioning movement is generated by the lifting device,
wherein the horizontal positioning movement is generated by the wheels of the equipment cart, and
wherein, when the X-ray receiver is moved toward a subject or away from the subject, the vertical positioning movement and the horizontal positioning movement of the C-arm is controlled in such a way that a position of the central axis is maintained in space.

2. The mobile X-ray device of claim 1, wherein the motion controller comprises a first drive controller configured to control a motorized drive of the lifting device to generate the vertical positioning movement of the C-arm, and a second drive controller configured to control a motorized drive of the wheels to generate the horizontal positioning movement of the C-arm.

3. The mobile X-ray device of claim 2, wherein the first drive controller actuates the motorized drive of the lifting device automatically while maintaining the space-fixed central axis, and
wherein the second drive controller actuates the motorized drive of the wheels automatically while maintaining the space-fixed central axis.

4. The mobile X-ray device of claim 2, wherein the first drive controller actuates the motorized drive of the lifting device automatically while maintaining the space-fixed central axis.

5. The mobile X-ray device of claim 2, wherein the second drive controller actuates the motorized drive of the wheels automatically while maintaining the space-fixed central axis.

6. A method for moving a mobile X-ray device, the method comprising:
providing the mobile X-ray device having: (1) an equipment cart that has wheels and a lifting device, (2) a support assembly arranged on the lifting device, (3) a C-arm mounted on the support assembly so as to be displaceable along a circumference of the support assembly, wherein the C-arm has an X-ray source and an X-ray receiver arranged opposite the X-ray source, and wherein a central axis extends between the X-ray source and the X-ray receiver for a given pose of the C-arm, and (4) a motion controller having at least one drive controller; and
controlling a movement of the C-arm, by the motion controller, such that the central axis extending between the X-ray source and the X-ray receiver is fixed in space for the given pose of the C-arm,
wherein the movement of the C-arm is a vertical positioning movement and a horizontal positioning movement of the C-arm,
wherein, when the X-ray receiver is moved toward a subject or away from the subject, the movement of the C-arm is controlled in such a way that a position of the central axis is maintained in space, and
wherein the at least one drive controller of the motion controller generates the vertical positioning movement of the C-arm by controlling a motorized drive of the lifting device and the at least one drive controller of the motion controller generates the horizontal positioning movement of the C-arm by controlling a motorized drive of the wheels.

7. The method of claim 6, wherein the motion controller actuates the motorized drive of the lifting device automatically while maintaining the space-fixed central axis.

8. The method of claim 7, wherein the motion controller actuates the motorized drive of the wheels automatically while maintaining the space-fixed central axis.

9. The method of claim 6, wherein the motion controller actuates the motorized drive of the wheels automatically while maintaining the space-fixed central axis.

10. A non-transitory electronically readable storage medium including a computer program that when executed, the non-transitory electronically readable storage medium and computer program configured to cause a computing device to perform:
- control a movement of a C-arm of a mobile X-ray device having (1) an equipment cart that has wheels and a lifting device, (2) a support assembly arranged on the lifting device, and (3) the C-arm mounted on the support assembly so as to be displaceable along a circumference of the support assembly, wherein the C-arm has an X-ray source and an X-ray receiver arranged opposite the X-ray source, and wherein a central axis extends between the X-ray source and the X-ray receiver for a given pose of the C-arm, such that the central axis extending between the X-ray source and the X-ray receiver is fixed in space for the given pose of the C-arm,
- wherein the movement of the C-arm is a vertical positioning movement and a horizontal positioning movement of the C-arm,
- wherein, when the X-ray receiver is moved toward a subject or away from the subject, the movement of the C-arm is controlled in such a way that a position of the central axis is maintained in space, and
- wherein the controller generates the vertical positioning movement of the C-arm by controlling a motorized drive of the lifting device and generates the horizontal positioning movement of the C-arm by controlling a motorized drive of the wheels.

* * * * *